United States Patent
Yamada

(10) Patent No.: US 10,198,875 B2
(45) Date of Patent: Feb. 5, 2019

(54) MAPPING IMAGE DISPLAY CONTROL DEVICE, METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/909,001

(22) Filed: Mar. 1, 2018

(65) Prior Publication Data

US 2018/0225884 A1 Aug. 9, 2018

Related U.S. Application Data

(63) Continuation of application No. PCT/JP2016/071554, filed on Jul. 22, 2016.

(30) Foreign Application Priority Data

Sep. 9, 2015 (JP) ................................ 2015-177524

(51) Int. Cl.
*G06T 19/20* (2011.01)
*A61B 6/03* (2006.01)
(Continued)

(52) U.S. Cl.
CPC ............... *G06T 19/20* (2013.01); *A61B 6/03* (2013.01); *A61B 6/50* (2013.01); *A61B 6/5211* (2013.01);
(Continued)

(58) Field of Classification Search
CPC . G06T 7/00; G06T 7/0012; G06T 7/11; G06T 7/13; G06T 7/149; G06T 19/20;
(Continued)

(56) References Cited

U.S. PATENT DOCUMENTS 7,822,461 B2 * 10/2010 Geiger .................. G06T 19/003
600/109
7,840,044 B2 * 11/2010 Ma ........................ G06T 7/0012
382/128

(Continued)

FOREIGN PATENT DOCUMENTS

JP 2011-212313 A 10/2011
JP 2012-45288 A 3/2012
(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2016/071554, dated Mar. 22, 2018, with English translation.

(Continued)

*Primary Examiner* — King Poon
*Assistant Examiner* — Vincent Peren
(74) *Attorney, Agent, or Firm* — Birch Stewart Kolasch & Birch LLP

(57) ABSTRACT

A mapping image display control device includes an organ region extraction unit that extracts an organ region from a three-dimensional-image, a tubular-structure-extraction unit that extracts a tubular structure in the organ region, a reaching-position-information-estimation unit that estimates pieces of reaching position information each of a position at which an extended line of a branch in the tubular structure reaches a surface of the organ region, a resection-region-information-acquisition unit that acquires information of a resection region in the organ region, a boundary-identifying-reaching-position-information-determination unit that determines pieces of boundary-identifying reaching position information used to identify a boundary of the resection region from among the pieces of reaching position information based on the information of the resection region, and a (Continued)

display-control unit that causes a mapping image in which the pieces of boundary-identifying reaching position information are mapped to the surface of the organ region to be displayed.

20 Claims, 16 Drawing Sheets

(51) Int. Cl.
    *A61B 6/00*     (2006.01)
    *G06T 7/11*     (2017.01)
    *G06T 7/13*     (2017.01)
    *G06T 7/149*     (2017.01)
    *G06T 7/00*     (2017.01)
    *G06T 17/00*     (2006.01)

(52) U.S. Cl.
    CPC .............. *G06T 7/0012* (2013.01); *G06T 7/11* (2017.01); *G06T 7/13* (2017.01); *G06T 7/149* (2017.01); *G06T 17/00* (2013.01); *A61B 6/032* (2013.01); *G06T 2207/10028* (2013.01); *G06T 2207/30061* (2013.01); *G06T 2219/2004* (2013.01)

(58) Field of Classification Search
    CPC . G06T 2207/10028; G06T 2207/30061; A61B 6/03; A61B 6/50; A61B 6/5211; A61B 6/032
    See application file for complete search history.

(56) References Cited

U.S. PATENT DOCUMENTS

| | | | |
|---|---|---|---|
| 8,150,138 B2 * | 4/2012 | Ohnishi | ................ G06T 7/0012 |
| | | | 382/134 |
| 9,603,668 B2 * | 3/2017 | Weingarten | ............. G06T 19/20 |
| 2011/0243403 A1 | 10/2011 | Mizuno | |
| 2012/0053443 A1 | 3/2012 | Sakuragi | |
| 2014/0079306 A1 | 3/2014 | Inoue | |
| 2015/0187118 A1 | 7/2015 | Masumoto | |

FOREIGN PATENT DOCUMENTS

| | | |
|---|---|---|
| JP | 2014-54428 A | 3/2014 |
| JP | 201473355 A | 4/2014 |

OTHER PUBLICATIONS

International Search Report (Form PCT/ISA/210) for International Application No. PCT/JP2016/071554, dated Oct. 18, 2016, with English translation.

Sato et al., "Thoracoscopic Wedge Lung Resection Using Virtual-Assisted Lung Mapping," Asian Cardiovascular and Thoracic Annals, vol. 0, No. 0, 2014 (published on web Jun. 12, 2014), pp. 1-9 (10 pages total).

* cited by examiner

MAPPING IMAGE DISPLAY CONTROL DEVICE, METHOD, AND PROGRAM

CROSS-REFERENCE TO RELATED APPLICATIONS

This application is a Continuation of PCT International Application No. PCT/JP2016/071554 filed on Jul. 22, 2016, which claims priority under 35 U.S.C § 119(a) to Japanese Patent Application No. 2015-177524 filed on Sep. 9, 2015. Each of the above application(s) is hereby expressly incorporated by reference, in its entirety, into the present application.

BACKGROUND OF THE INVENTION

1. Field of the Invention

The present invention relates to a device, method, and a computer readable non-transitory recording medium storing a program for simulating positions on the lung surface at which dye seeps if the dye is sprayed to the peripheries of bronchi and for generating and displaying a mapping image in which the positions are mapped to the lung surface.

2. Description of the Related Art

VAL-MAP (Virtual Assisted Lung Mapping) has been recently proposed as a method for marking a resection region of the lung (see Masaaki Sato and eight others, "Thoracoscopic wedge lung resection using virtual-assisted lung mapping", [online], Jun. 12, 2014, Asian Cardiovascular and Thoracic Annals, <URL:http://aan.sagepub.com/content/early/2014/06/12/0218492314539332>). In VAL-MAP, each bronchus located near a tumor is selected in a given manner and a bronchoscopic procedure is performed in the bronchus. A catheter is advanced up to the periphery of the bronchus, and dye is sprayed to stain the lung surface.

Staining the lung surface in this way enables highly accurate prediction of the location of a tumor by using the stained regions as landmarks at the time of a procedure of thoracotomy or thoracoscopy.

SUMMARY OF THE INVENTION

When performing VAL-MAP described above, doctors sometimes desire to confirm which bronchus is to be selected for dye spraying in order to appropriately resect a tumor, through a simulation prior to the procedure. Accordingly, methods for simulating stainable positions on the lung surface on the basis of bronchus regions extracted by image processing and for determining each bronchus that is to be selected in order to appropriately resect a tumor on the basis of the simulated positions are conceivable.

As a simulation method, there is a method for extending a bronchus region to the lung surface and setting the position at which the extended line reaches the lung surface as a to-be-stained position since the bronchus region usually does not extend to be in contact with the lung surface.

However, even if to-be-stained positions can be confirmed by the above-described simulation, each bronchus that is to be selected in order to appropriately resect a tumor needs to be determined by taking into account a depth direction of the tumor, etc. That is, each bronchus needs to be carefully selected while changing a displayed state of a three-dimensional mapping image in which to-be-stained positions are mapped, such as while rotating the three-dimensional mapping image. This requires time.

In view of the circumstance described above, an object of the present invention is to provide a mapping image display control device, method, and a computer readable non-transitory recording medium storing a program that can reduce time taken for the work by automatically determining to-be-stained positions corresponding to respective bronchi that are to be selected in order to appropriately resect a tumor or the like from among to-be-stained positions on the lung surface that are determined by a simulation.

A mapping image display control device according to an aspect of the present invention includes an organ region extraction unit that extracts an organ region included in a three-dimensional image, a tubular structure extraction unit that extracts a tubular structure included in the organ region, a reaching position information estimation unit that estimates pieces of reaching position information each of a position at which an extended line of a branch included in the tubular structure reaches a surface of the organ region, a resection region information acquisition unit that acquires information of a resection region in the organ region, a boundary-identifying reaching position information determination unit that determines pieces of boundary-identifying reaching position information used to identify a boundary of the resection region from among the pieces of reaching position information based on the information of the resection region, and a display control unit that generates a mapping image in which the pieces of boundary-identifying reaching position information are mapped to the surface of the organ region and that causes a display unit to display the mapping image.

In addition, in the mapping image display control device according to the aspect of the present invention, the boundary-identifying reaching position information determination unit can determine pieces of reaching position information of positions located in a previously set range from the boundary of the resection region on the surface of the organ region as the pieces of boundary-identifying reaching position information.

In addition, in the mapping image display control device according to the aspect of the present invention, the boundary-identifying reaching position information determination unit can determine a predetermined number of pieces of reaching position information in ascending order of distance from the boundary of the resection region on the surface of the organ region as the pieces of boundary-identifying reaching position information.

In addition, in the mapping image display control device according to the aspect of the present invention, the boundary-identifying reaching position information determination unit can determine pieces of reaching position information of positions located inside the resection region as the pieces of boundary-identifying reaching position information.

In addition, in the mapping image display control device according to the aspect of the present invention, the boundary-identifying reaching position information determination unit can determine, as the pieces of boundary-identifying reaching position information, three or more pieces of reaching position information for which an area of a polygonal shape formed by linking positions indicated by the three or more pieces of reaching position information is the largest among pieces of reaching position information of positions located inside the resection region on the surface of the organ region.

In addition, in the mapping image display control device according to the aspect of the present invention, the resection region information acquisition unit can extract a lesion region included in the organ region and can acquire the information of the resection region based on the lesion region.

In addition, in the mapping image display control device according to the aspect of the present invention, the resection region information acquisition unit can determine a dominated region of a branch included in the tubular structure and can acquire the information of the resection region based on the dominated region.

In addition, in the mapping image display control device according to the aspect of the present invention, the display control unit can set a region including a reaching position identified by each of the pieces of boundary-identifying reaching position information, can generate a mapping image in which the region is mapped to the surface of the lung region, and can cause the display unit to display the mapping image.

In addition, in the mapping image display control device according to the aspect of the present invention, a lung region can be extracted as the organ region, and a bronchus region can be extracted as the tubular structure.

In addition, the mapping image display control device according to the aspect of the present invention can include a branching position information acquisition unit that acquires information of a branching position of the tubular structure, and the reaching position information estimation unit can estimate each of the pieces of reaching position information based on the information of the branching position.

A mapping image display control method according to an aspect of the present invention includes extracting an organ region included in a three-dimensional image, extracting a tubular structure included in the organ region, estimating pieces of reaching position information each of a position at which an extended line of a branch included in the tubular structure reaches a surface of the organ region, acquiring information of a resection region in the organ region, determining pieces of boundary-identifying reaching position information used to identify a boundary of the resection region from among the pieces of reaching position information based on the information of the resection region, and generating a mapping image in which the pieces of boundary-identifying reaching position information are mapped to the surface of the organ region and causing a display unit to display the mapping image.

A computer readable non-transitory recording medium storing a mapping image display control program according to an aspect of the present invention causes a computer to function as an organ region extraction unit that extracts an organ region included in a three-dimensional image, a tubular structure extraction unit that extracts a tubular structure included in the organ region, a reaching position information estimation unit that estimates pieces of reaching position information each of a position at which an extended line of a branch included in the tubular structure reaches a surface of the organ region, a resection region information acquisition unit that acquires information of a resection region in the organ region, a boundary-identifying reaching position information determination unit that determines pieces of boundary-identifying reaching position information used to identify a boundary of the resection region from among the pieces of reaching position information based on the information of the resection region, and a display control unit that generates a mapping image in which the pieces of boundary-identifying reaching position information are mapped to the surface of the organ region and that causes a display unit to display the mapping image.

With the mapping image display control device, method, and computer readable non-transitory recording medium storing a program according to the aspects of the present invention, an organ region included in a three-dimensional image is extracted, a tubular structure included in the organ region is extracted, and pieces of reaching position information each of a position at which an extended line of a branch included in the tubular structure reaches the surface of the organ region are estimated. With this configuration, in the case where a bronchus region is extracted as the tubular structure, for example, a position on the lung surface that is to be stained if dye is sprayed to the periphery of a branch of the bronchus can be acquired as the piece of reaching position information described above.

Further, information of a resection region in the organ region is acquired, pieces of boundary-identifying reaching position information used to identify a boundary of the resection region are determined from among the above-described pieces of reaching position information based on the information of the resection region, and a mapping image in which the pieces of boundary-identifying reaching position information are mapped to the surface of the organ region is generated and displayed on a display unit. With this configuration, since to-be-stained positions corresponding to respective bronchi that are to be selected in order to appropriately resect a tumor or the like can be automatically determined as pieces of boundary-identifying reaching position information from among to-be-stained positions (pieces of reaching position information) on the lung surface that are determined by a simulation, the user's time for the work can be reduced.

DESCRIPTION OF THE PREFERRED EMBODIMENTS

Figure 1:
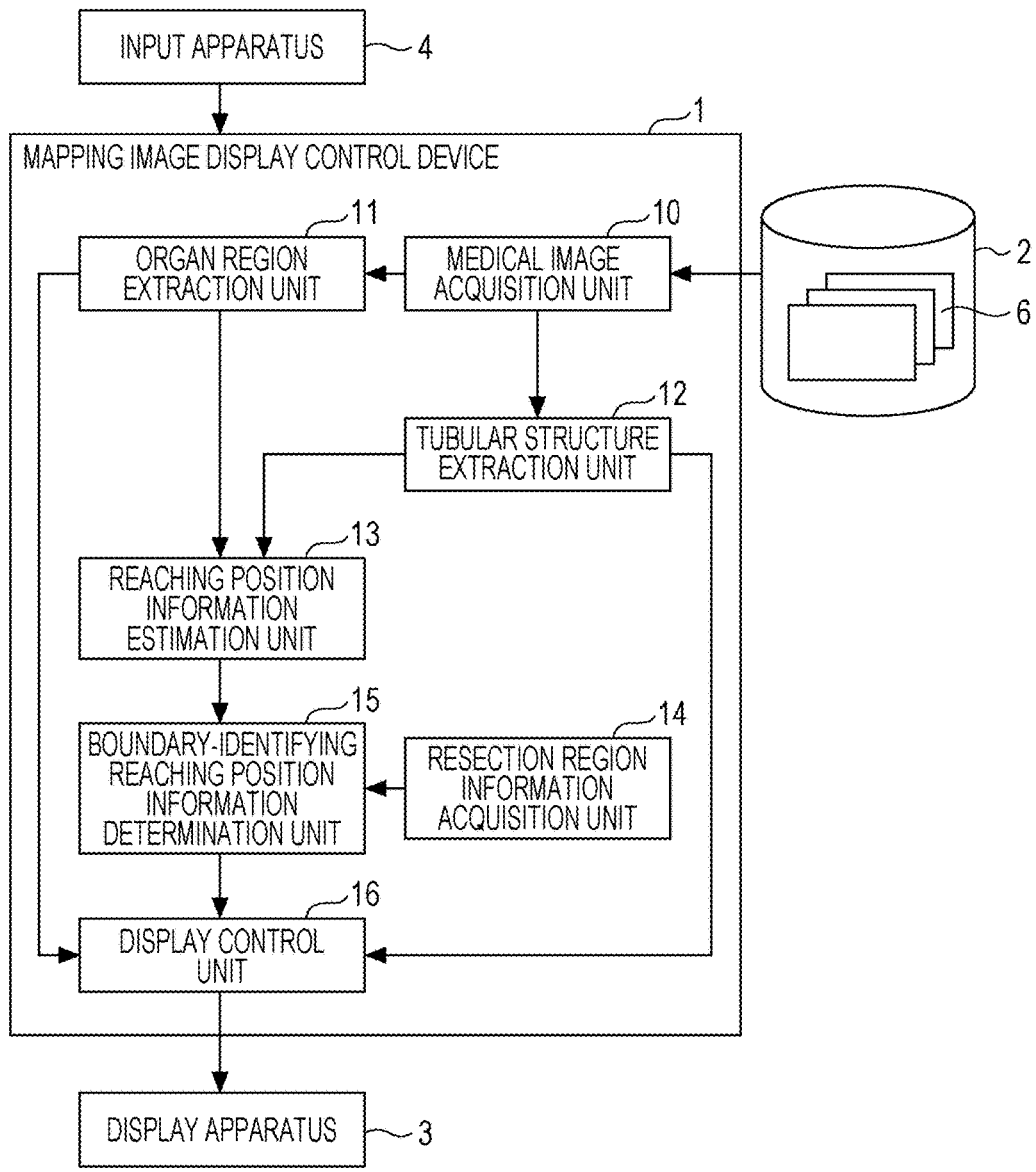
FIG. 1 is a block diagram illustrating a schematic configuration of a medical-image-diagnosis assisting system that uses an embodiment of a mapping image display control device, method, and computer readable non-transitory recording medium storing a program according to the present invention.

A medical-image-diagnosis assisting system that uses an embodiment of a mapping image display control device, method, and computer readable non-transitory recording medium storing a program according to the present invention will be described in detail below with reference to the drawings. FIG. 1 is a block diagram illustrating a schematic configuration of the medical-image-diagnosis assisting system according to the embodiment.

The medical-image-diagnosis assisting system according to the embodiment assists doctors when the doctors perform VAL-MAP described above. Specifically, the medical-image-diagnosis assisting system according to the embodiment simulates positions on the lung surface at which dye seeps if the dye is sprayed to the peripheries of individual bronchi, automatically determines positions for identifying a boundary of a resection region in the lung from among the positions, generates a mapping image in which the positions are mapped, and displays the generated mapping image. Doctors are able to appropriately select bronchi in which the dye is to be sprayed by observing the mapping image before performing the procedure.

Specifically, as illustrated in FIG. 1, the medical-image-diagnosis assisting system according to the embodiment includes a mapping image display control device 1, a medical image storage server 2, a display apparatus 3 (corresponding to a display unit), and an input apparatus 4.

The mapping image display control device 1 is implemented by installing the mapping image display control program according to the embodiment on a computer.

The mapping image display control device 1 includes a CPU (central processing unit), a semiconductor memory, and a storage device such as a hard disk or an SSD (solid state drive). The mapping image display control program according to the embodiment is installed on the storage device. As a result of this mapping image display control program being executed by the CPU, a medical image acquisition unit 10, an organ region extraction unit 11, a tubular structure extraction unit 12, a reaching position information estimation unit 13, a resection region information acquisition unit 14, a boundary-identifying reaching position information determination unit 15, and a display control unit 16 illustrated in FIG. 1 operate.

The mapping image display control program is distributed after being recorded on a recording medium, such as a DVD (Digital Versatile Disc) or a CD-ROM (Compact Disc Read Only Memory), and is installed on the computer from the recording medium. Alternatively, the mapping image display control program is stored in a storage device of a server computer connected to a network or a network storage in an externally accessible state and is downloaded to and installed on the computer in response to a request.

The medical image acquisition unit 10 acquires three-dimensional images 6 of patients obtained by imaging the patients in advance. The three-dimensional images 6 are obtained by imaging patients by using a CT (computed tomography) apparatus or an MM (magnetic resonance imaging) apparatus, for example. In the embodiment, a case of acquiring the three-dimensional image 6 of the thorax of a patient is described.

The three-dimensional images 6 are stored in the medical image storage server 2 in advance, together with identification information of respective patients. On the basis of identification information of a patient input by the user by using the input apparatus 4 or the like, the medical image acquisition unit 10 reads out the three-dimensional image 6 having the identification information from the medical image storage server 2 and temporarily stores the three-dimensional image 6.

The organ region extraction unit 11 performs a process of extracting a lung region from the three-dimensional image 6 of the thorax acquired by the medical image acquisition unit 10. As a method for extracting a lung region, a publicly known method, such as a method for extracting a lung region by creating a histogram of signal values at respective pixel positions in the three-dimensional image 6 and processing the histogram using a threshold or a region growing method based on seed points representing a lung region, can be used since the lung fields are regions where air is present.

The tubular structure extraction unit 12 performs a process of extracting a bronchus region included in the lung region of the three-dimensional image 6 of the thorax. Bronchi included in the three-dimensional image 6 are assumed such that pixels for the inside of the bronchi are represented as regions showing low pixel values since they correspond to an air region but the bronchus walls are structures having a cylindrical column shape or a linear shape that show relatively high pixel values. Thus, a structural analysis of a shape based on a pixel value distribution is performed for individual pixels to extract bronchi. For example, as in a method described in JP2012-200403A, a bronchus region and a graph structure obtained by performing thinning on the bronchus region can be extracted by performing Hessian analysis based on pixel values of respective pixels. Note that another publicly known technique may be used as the method for extracting a bronchus region.

The reaching position information estimation unit 13 estimates pieces of reaching position information each about a position at which an extended line of a branch included in a bronchus region reaches the surface of the lung region on the basis of the graph structure of the bronchus region extracted by the tubular structure extraction unit 12.

A position at which, if dye is sprayed to the periphery of a bronchus in VAL-MAP, the dye reaches the lung surface and seeps to the lung surface after passing through the lung tissue can be estimated as a position at which the extended line of the branch of the bronchus reaches the lung surface.

Accordingly, the reaching position information estimation unit 13 according to the embodiment sets a straight line that links the end of a branch included in a graph structure of a bronchus region and a point on an edge near the end (for example, a point immediately preceding the end) as an extended line of the branch and estimates a position at which the extended line reaches the surface of the lung region as a position which the dye reaches (seeps).

Figure 2:
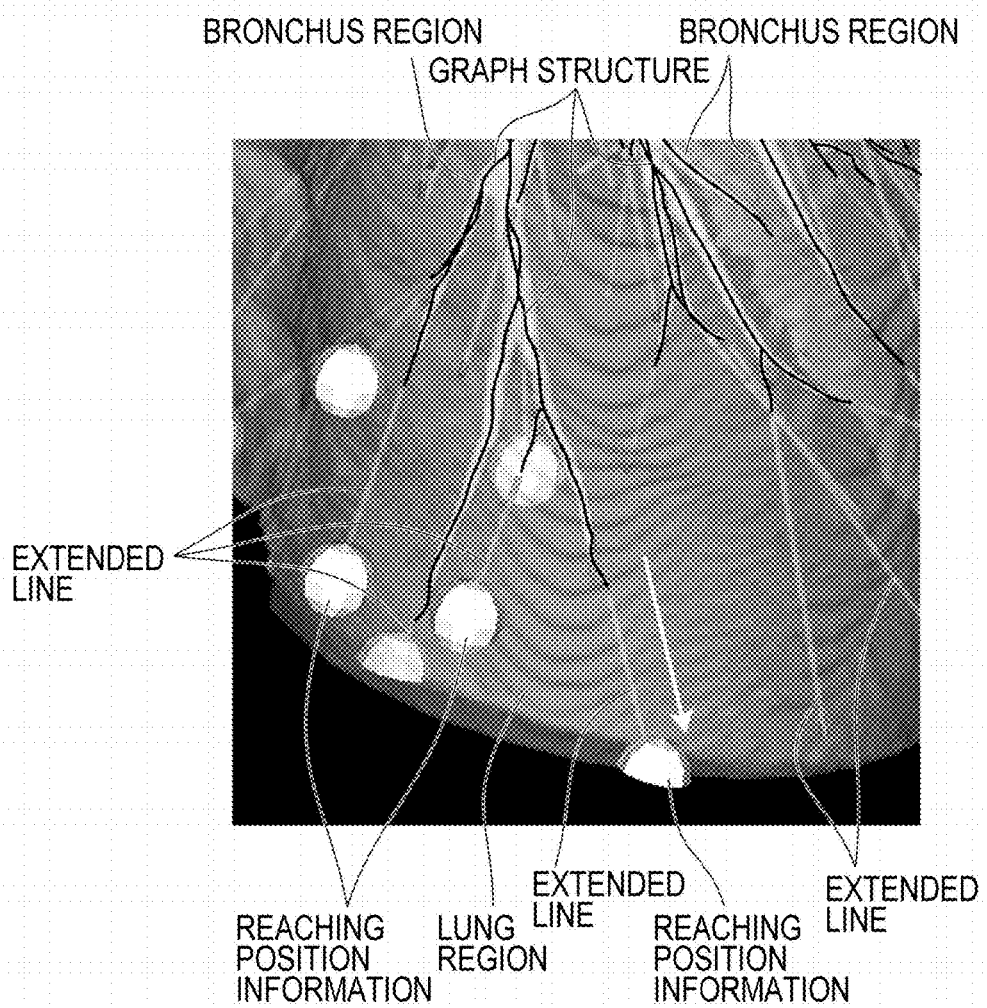
FIG. 2 is a diagram illustrating an example of a mapping image in which pieces of reaching position information are superimposed on a volume rendering image of a lung region and bronchus regions.

FIG. 2 illustrates a volume rendering image of a lung region and bronchus regions. FIG. 2 also illustrates the graph structures of the bronchus regions by using thin black lines and extended lines of branches of the graph structures by using thick gray lines. FIG. 2 further illustrates pieces of reaching position information about positions at which respective extended lines of the branches of the graph structures reach the surface of the lung region by using spheres or hemispheres.

Note that an intersection of an extended line of a branch of a bronchus region and the surface of the lung region may be acquired as a piece of reaching position information, or a two-dimensional or three-dimensional range including the intersection may be acquired as a piece of reaching position information. A piece of reaching position information is information representing a reaching point or reaching range at which, if dye is sprayed to the periphery of a bronchus, the dye reaches the lung surface after passing through the lung tissue.

Figure 3:
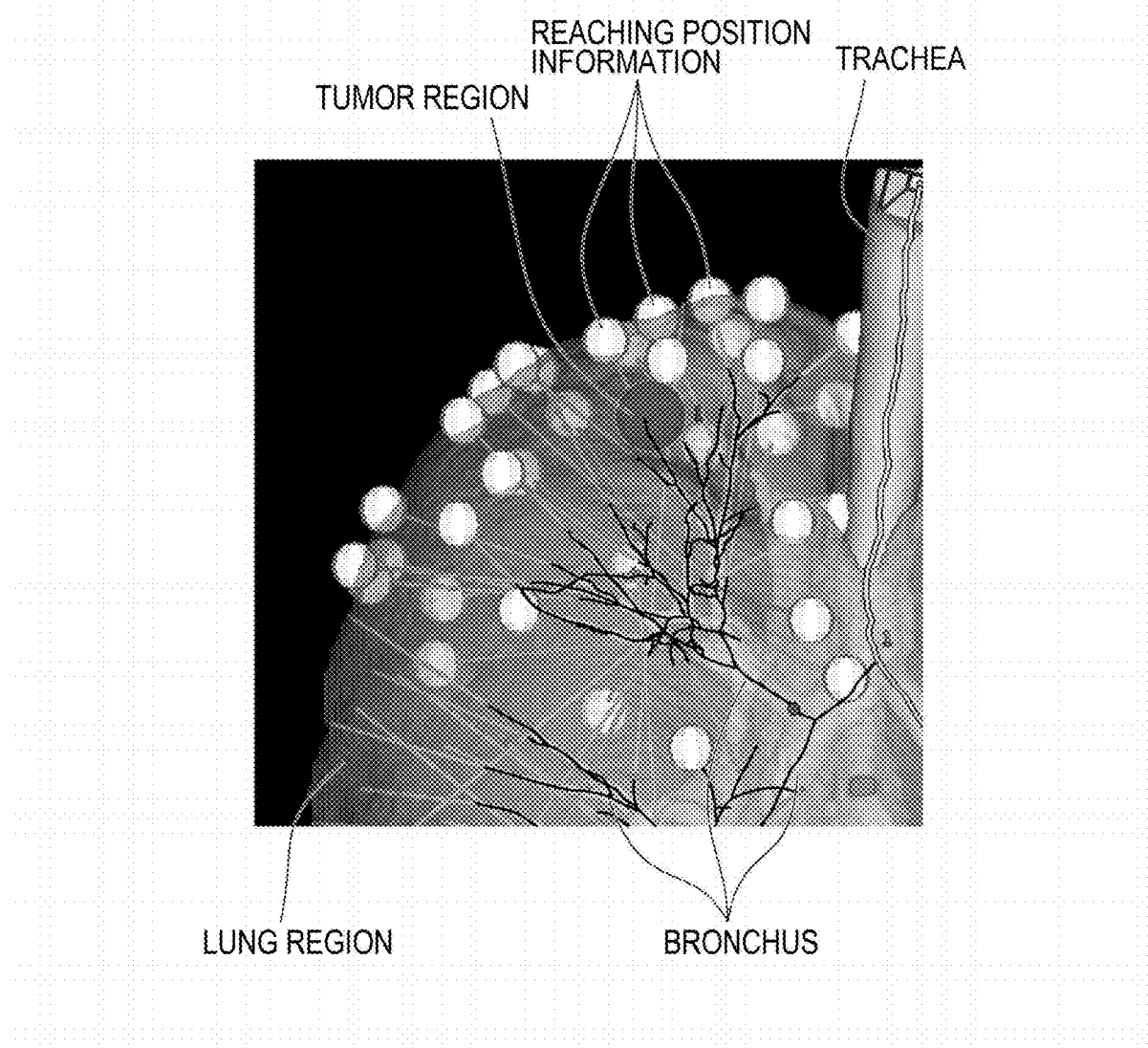
FIG. 3 is a diagram illustrating an example of a tumor region in the lung region.

The resection region information acquisition unit 14 acquires information about a resection region in the lung region extracted by the organ region extraction unit 11. Specifically, if a tumor region is present in the lung region as illustrated in FIG. 3, for example, the resection region information acquisition unit 14 according to the embodiment acquires information about a resection region including the tumor region. Note that the resection region is a to-be-resected region that is set in a three-dimensional image of an organ in the case where a lesion portion is resected from the organ, such as the lung, by a surgery.

Figure 4:
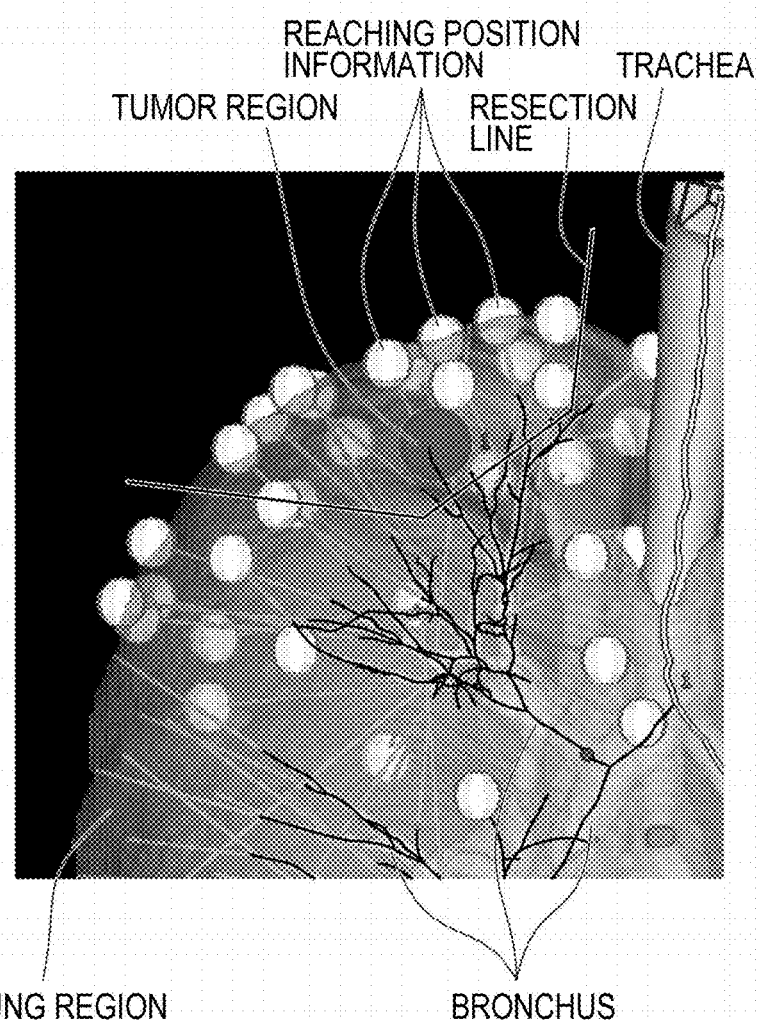
FIG. 4 is a diagram illustrating an example of a resection line that is set and input by a user.

In the embodiment, the user sets and inputs a resection region including a tumor region by using the input apparatus 4 in a state in which an image such as a volume rendering image of the lung region, the bronchus regions, and the tumor region is displayed on the display apparatus 3 as illustrated in FIG. 4. Information about the set and input resection region is acquired by the resection region information acquisition unit 14.

Figure 5:
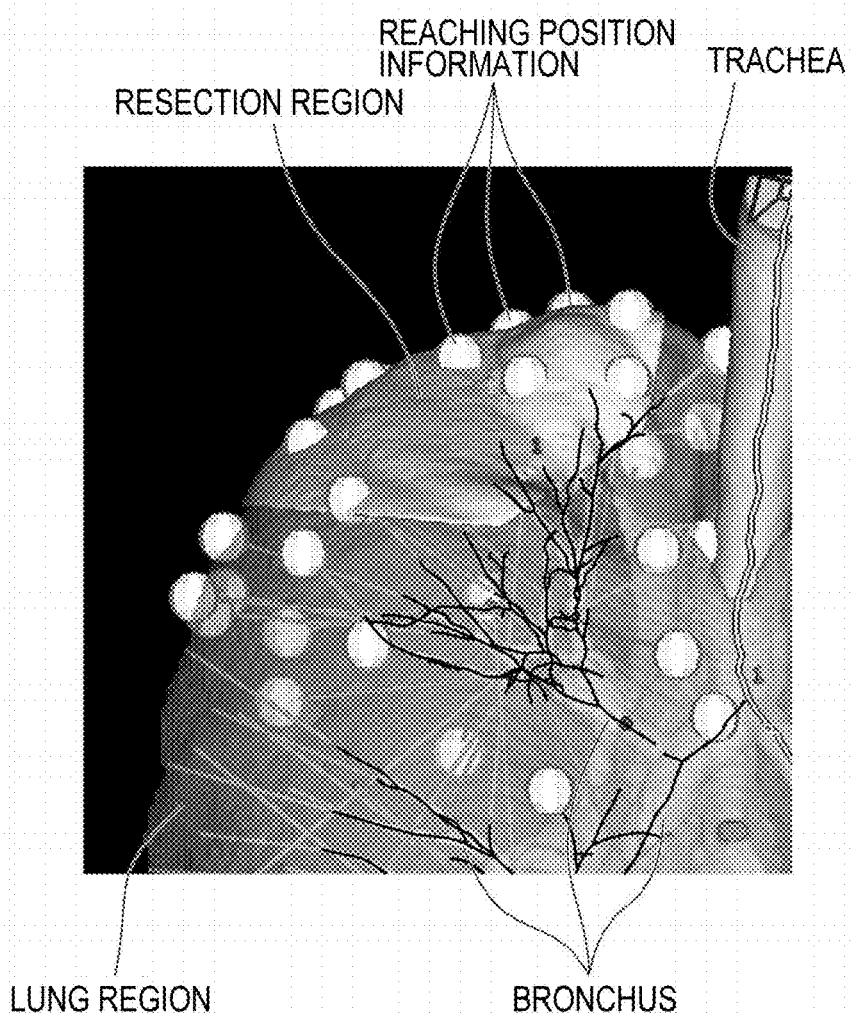
FIG. 5 is a diagram illustrating the surface of a resection region that is three-dimensionally set and input.

As a resection region set/input method, an input for setting a resection line may be received as illustrated in FIG. 4, for example. Since the display coordinate system of the display apparatus 3 is two-dimensional, an input for setting a depth direction is not possible. However, a plane formed by projecting the resection line in a direction perpendicular to a projection plane of the volume rendering image can be treated as a boundary plane of the resection region. That is, a three-dimensional resection region can be set and input by setting and inputting the resection line illustrated in FIG. 4. FIG. 5 illustrates the surface of the resection region that is three-dimensionally set and input. Note that the resection line may be set using a straight line as described above or may be set using a curved line.

The boundary-identifying reaching position information determination unit 15 determines pieces of boundary-identifying reaching position information that are used to identify the boundary of the resection region from among the pieces of reaching position information acquired by the reaching position information estimation unit 13, on the basis of the information about the resection region acquired by the resection region information acquisition unit 14.

Figure 6:
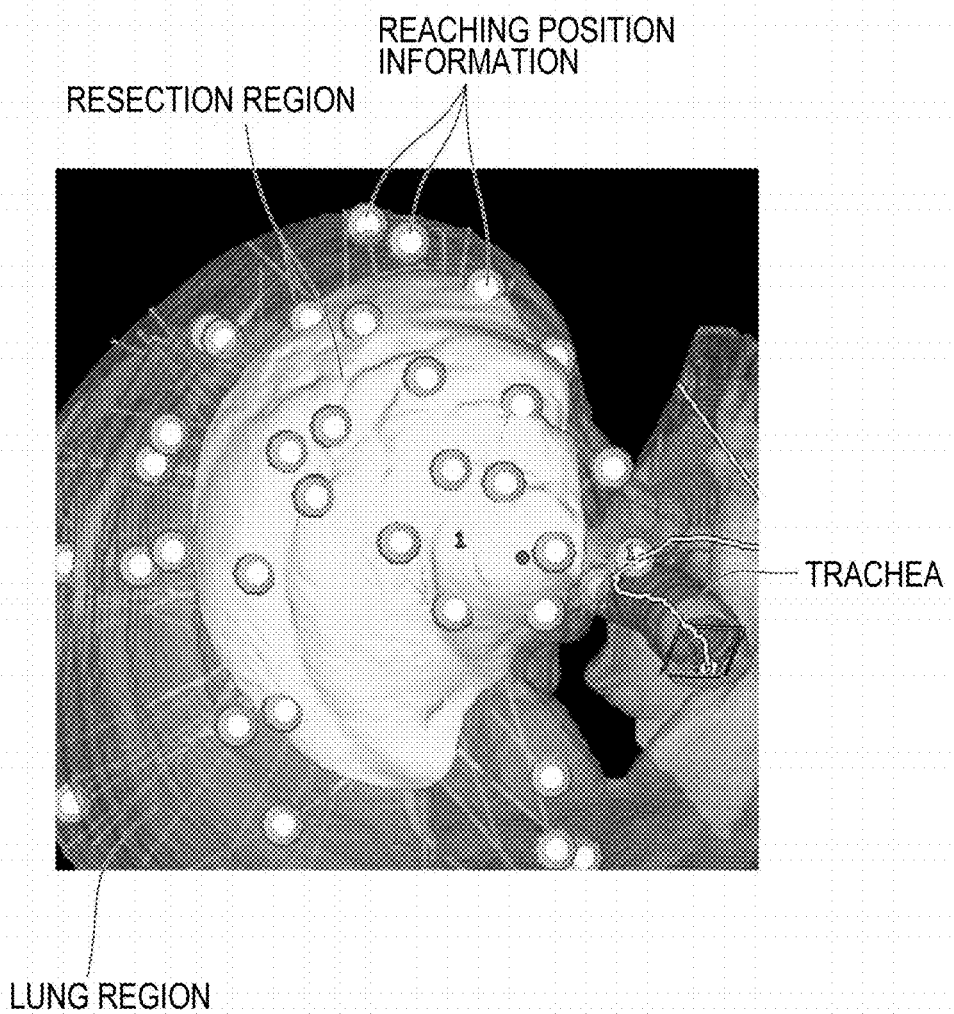
FIG. 6 is a diagram in which the surface of the resection region on the surface of the lung region is turned to the front direction.
Figure 7:
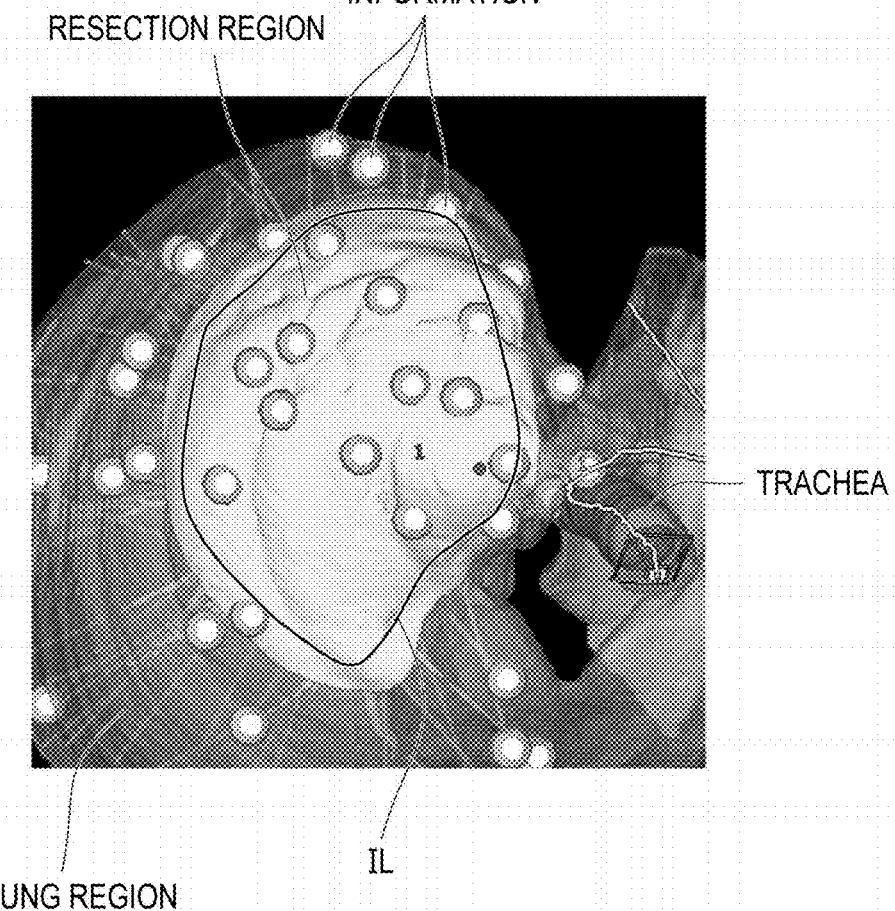
FIG. 7 is a diagram for describing a method for determining pieces of boundary-identifying reaching position information.
Figure 8:
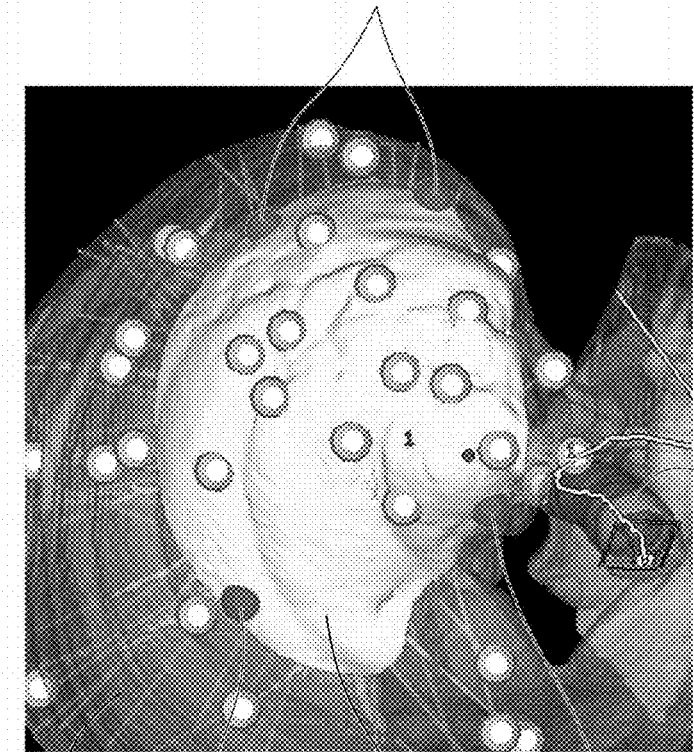
FIG. 8 is a diagram illustrating an example of pieces of boundary-identifying reaching position information.

FIGS. 6 and 7 are diagrams in which the surface of the resection region on the surface of the lung region is turned to the front direction. The boundary-identifying reaching position information determination unit 15 according to the embodiment identifies a boundary (outline) of the resection region on the surface of the lung region and sets a line IL located on the inner side of the boundary by a previously set width as illustrated in FIG. 7. The boundary-identifying reaching position information determination unit 15 then determines pieces of reaching position information located in a range between the boundary and the line IL as pieces of boundary-identifying reaching position information from among the plurality of pieces of reaching position information estimated by the reaching position information estimation unit 13. FIG. 8 illustrates an example of the pieces of boundary-identifying reaching position information determined in the above-described manner. FIG. 8 illustrates the pieces of boundary-identifying reaching position information by using a color different from a color for the other pieces of reaching position information. Note that the width used to set the line IL may be set by the user in a given manner by using the input apparatus 4. In addition, the line IL may be determined by reducing the resection region by a previously set percentage. As described above, in the case where pieces of reaching position information about positions located in a range between the boundary of the resection region and the line IL are determined as pieces of boundary-identifying reaching position information, the pieces of boundary-identifying reaching position information can be determined through a simple process.

The display control unit 16 generates a volume rendering image of the lung region and the bronchus regions on the basis of the lung regions extracted by the organ region extraction unit 11 and the bronchus regions extracted by the tubular structure extraction unit 12. Opacity of the volume rendering image of the lung region is set such that the bronchus regions in the lung region are visually recognizable, and the color for the lung region and the color for the bronchus regions are set to be different.

In addition, the display control unit 16 causes the display apparatus 3 to display a mapping image in which the graph structures obtained by performing thinning on the bronchus regions and the extended lines of the branches of the bronchus regions and pieces of reaching position information set by the reaching position information estimation unit 13 are superimposed onto the volume rendering image of the lung region and the bronchus regions. FIG. 8 illustrates an example of the mapping image. The pieces of boundary-identifying reaching position information are displayed in a manner different from that of the other pieces of reaching position information. For example, the pieces of boundary-identifying reaching position information and the other pieces of reaching position information are displayed using different colors as illustrated in FIG. 8. However, the display manner is not limited to this one, and the pieces of boundary-identifying reaching position information and the other pieces of reaching position information may be displayed in different shapes, or the pieces of boundary-identifying reaching position information may be displayed to flash on and off. In addition, display and non-display may be switched between such that the pieces of reaching position information other than the pieces of boundary-identifying reaching position information are not displayed.

In addition, the size of the sphere or hemisphere representing each piece of reaching position information and displayed in the mapping image can be set by the user in a given manner by using the input apparatus 4. In addition, the extended lines of the bronchus regions need not necessarily be displayed, and display and non-display may be switched between by the user.

In addition, the display control unit 16 is capable of displaying and rotating the volume rendering image of the lung region or the like in response to receipt of an instruction from the user. Thus, the display control unit 16 is capable of displaying the branches of the bronchus regions corresponding to the respective pieces of boundary-identifying reaching position information by rotating the volume rendering image illustrated in FIG. 8. As a result, the user is able to confirm the branches of the bronchus regions corresponding to the respective pieces of boundary-identifying reaching position information and to select the branches of the bronchus regions in which dye is to be sprayed. Note that a display manner of the branches of the bronchus regions corresponding to the pieces of boundary-identifying reaching position information may be set differently from that of the other branches so as to allow the user to easily confirm the branches in which dye is to be sprayed. For example, the branches of the bronchus regions corresponding to the pieces of boundary-identifying reaching position information may be displayed using a different color or may be displayed to flash on and off.

The display apparatus 3 includes a display device such as a liquid crystal display. The display apparatus 3 displays the above-described volume rendering image or the like.

The input apparatus 4 receives various inputs for setting from the user and includes input devices such as a keyboard and a mouse. The input apparatus 4 receives, for example, an input for setting identification information of a patient, an input for setting the opacity and color of the volume rendering image, an input for setting a resection region in the lung region, and an input for setting the displayed shape and size of pieces of reaching position information.

Note that a touch panel may be used as both the display apparatus 3 and the input apparatus 4.

Figure 9:
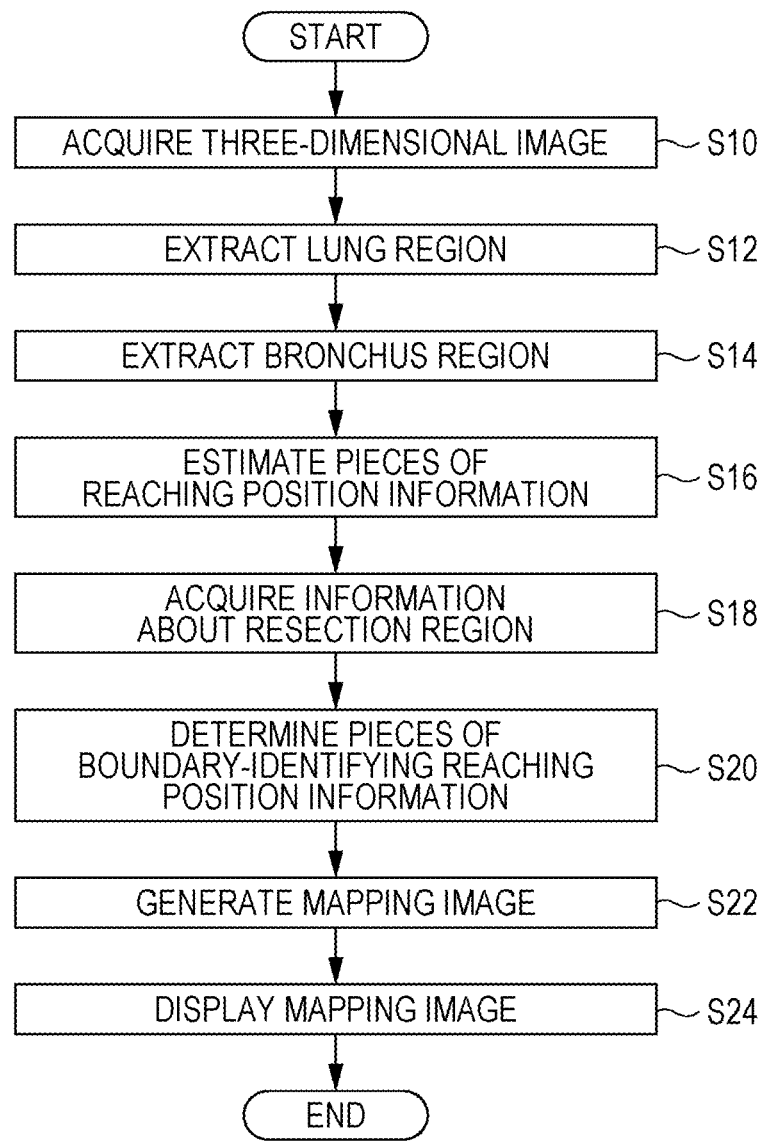
FIG. 9 is a flowchart for describing an operation of the medical-image-diagnosis assisting system that uses an embodiment of the mapping image display control device, method, and computer readable non-transitory recording medium storing a program according to the present invention.

An operation of the medical-image-diagnosis assisting system according to the embodiment will be described next with reference to a flowchart illustrated in FIG. 9.

First, the medical image acquisition unit 10 reads out and acquires the three-dimensional image 6 from the medical image storage server 2 in accordance with identification information of a patient or the like input by the user (S10).

The three-dimensional image 6 acquired by the medical image acquisition unit 10 is input to the organ region extraction unit 11 and the tubular structure extraction unit 12. The organ region extraction unit 11 extracts each lung region from the input three-dimensional image 6 (S12). The tubular structure extraction unit 12 extracts bronchus regions from the input three-dimensional image 6 and further acquires graph structures obtained by performing thinning on the bronchus regions (S14).

The graph structures acquired by the tubular structure extraction unit 12 are input to the reaching position information estimation unit 13. The reaching position information estimation unit 13 sets extended lines of branches of the bronchus regions on the basis of the graph structures and acquires pieces of information about intersections of the respective extended lines and the surface of the lung region as pieces of reaching position information (S16).

Then, the user sets and inputs the resection region by using the input apparatus 4 in a state in which an image such as a volume rendering image of the lung region, the bronchus regions, and the tumor region is displayed on the display apparatus 3. Information about the set and input resection region is acquired by the resection region information acquisition unit 14 (S18).

The information about the resection region acquired by the resection region information acquisition unit 14 is input to the boundary-identifying reaching position information determination unit 15. The boundary-identifying reaching position information determination unit 15 determines pieces of boundary-identifying reaching position information that are used to identify the boundary of the resection region from among the pieces of the reaching position information on the basis of the input information about the resection region in a manner as described above (S20).

Then, the display control unit 16 generates a mapping image in which the pieces of reaching position information are superimposed on the surface of the lung region (S22). The mapping image is then displayed on the display apparatus 3 (S24). At that time, the pieces of boundary-identifying reaching position information are displayed in a manner different from that of the other pieces of reaching position information.

With the medical-image-diagnosis assisting system according to the embodiment, information about a resection region of the lung region is acquired. On the basis of the information about the resection region, pieces of boundary-identifying reaching position information that are used to identify a boundary of the resection region are determined from among pieces of reaching position information described above. A mapping image in which the pieces of boundary-identifying reaching position information are mapped to the surface of the lung region is generated and displayed on the display apparatus 3. In this way, to-be-stained positions corresponding to bronchi that are to be selected in order to appropriately resect a tumor or the like can be automatically determined as pieces of boundary-identifying reaching position information from among to-be-stained positions (pieces of reaching position information) on the lung surface that are determined by a simulation. Thus, the user's time for the work can be reduced.

Note that the method for determining pieces of boundary-identifying reaching position information is not limited to the method described above. For example, a predetermined number of pieces of reaching position information in ascending order of distance from the boundary of the resection region on the surface of the lung region may be determined as pieces of boundary-identifying reaching position information. Specifically, a distance between the boundary of the resection region and a position indicated by each piece of reaching position information is calculated, and the top three pieces of reaching position information in ascending order of distance may be determined as pieces of boundary-identifying reaching position information. Note that the predetermined number may be set by the user in a given manner by using the input apparatus 4. As described above, in the case where pieces of boundary-identifying reaching position information are determined in ascending order of distance from the boundary of the resection region, pieces of reaching position information of positions that are closer to the boundary of the resection region can be preferentially determined as the pieces of boundary-identifying reaching position information.

In addition, in the case where pieces of reaching position information of positions that are closer to the boundary of the resection region are determined as pieces of boundary-identifying reaching position information as described above, it is desirable to determine pieces of reaching position information of positions that are present inside the resection region as the pieces of boundary-identifying reaching position information. That is, it is desirable that if a position indicated by a piece of reaching position information is located closely to the boundary of the resection region but is located outside the resection region, such a piece of reaching position information is not determined as a piece of boundary-identifying reaching position information; instead, a position indicated by a piece of reaching position information that is located closely to the boundary of the resection region and is located inside the resection region is determined as a piece of boundary-identifying reaching position information.

In addition, three or more pieces of reaching position information for which an area of a polygonal shape formed by linking positions indicated by the three or more pieces of reaching position information is the largest among pieces of reaching position information of positions located in the resection region on the surface of the lung region may be determined as pieces of boundary-identifying reaching position information. Specifically, all the combinations of three or more pieces of reaching position information among a plurality of pieces of reaching position information of positions located in the resection region are set, and the area of a polygonal shape formed by each of the combinations is calculated. Then, pieces of reaching position information of the combination that forms the polygonal shape having the largest area among the polygonal shapes formed by the respective combinations may be determined as pieces of boundary-identifying reaching position information. Note that a polygonal shape formed by a combination of three or more pieces of reaching position information is a polygonal shape that has positions indicated by the three or more pieces of reaching position information as apices thereof and that is formed by linking the positions indicated by the pieces of reaching position information to each other by straight lines. In the case where the pieces of boundary-identifying reaching position information are determined in this manner, pieces of reaching position information that form a polygonal shape close to the shape of the resection region can be determined as pieces of boundary-identifying reaching position information.

In addition, the resection region is manually set by the user in the embodiment described above. However, the resection region information acquisition unit 14 may automatically set the resection region. For example, the resection region information acquisition unit 14 may extract a lesion region, such as a tumor region, in the lung region and may set the resection region on the basis of the lesion region. Various publicly known techniques can be used as the lesion region extraction method. In addition, a region that includes a lesion region and for which an area of the range of the resection region on the lung surface is greater than or equal to a previously set size is set as the resection region. When the resection region is automatically set in this way, the user's time can be further reduced.

The method for automatically setting the resection region is not limited to the method described above. For example, a dominated region of a branch included in a bronchus region may be determined, and a resection region may be automatically set on the basis of the dominated region. Specifically, a lesion region, such as a tumor region, in the lung region is extracted, and a branch whose distance to the lesion region is less than or equal to a previously set threshold is identified. Then, a dominated region of the branch is identified, and the dominated region may be set as the resection region. Note that a dominated region is set in advance for each branch from the anatomical viewpoint.

In addition, in the embodiment described above, an extended line of a branch of a bronchus region is set on the basis of a graph structure acquired from the bronchus region. However, for example, the end of the branch sometimes has an irregular shape depending on the extraction accuracy of the graph structure. In such cases, if a straight line that links the end of the branch and the point on the edge near the end is set as an extended line in a manner as described above, the extending direction of the extended line sometimes completely differs from the actual extending direction of the branch of the bronchus region. As a result, the estimation accuracy of the reaching position of the dye may decrease.

Figure 10:
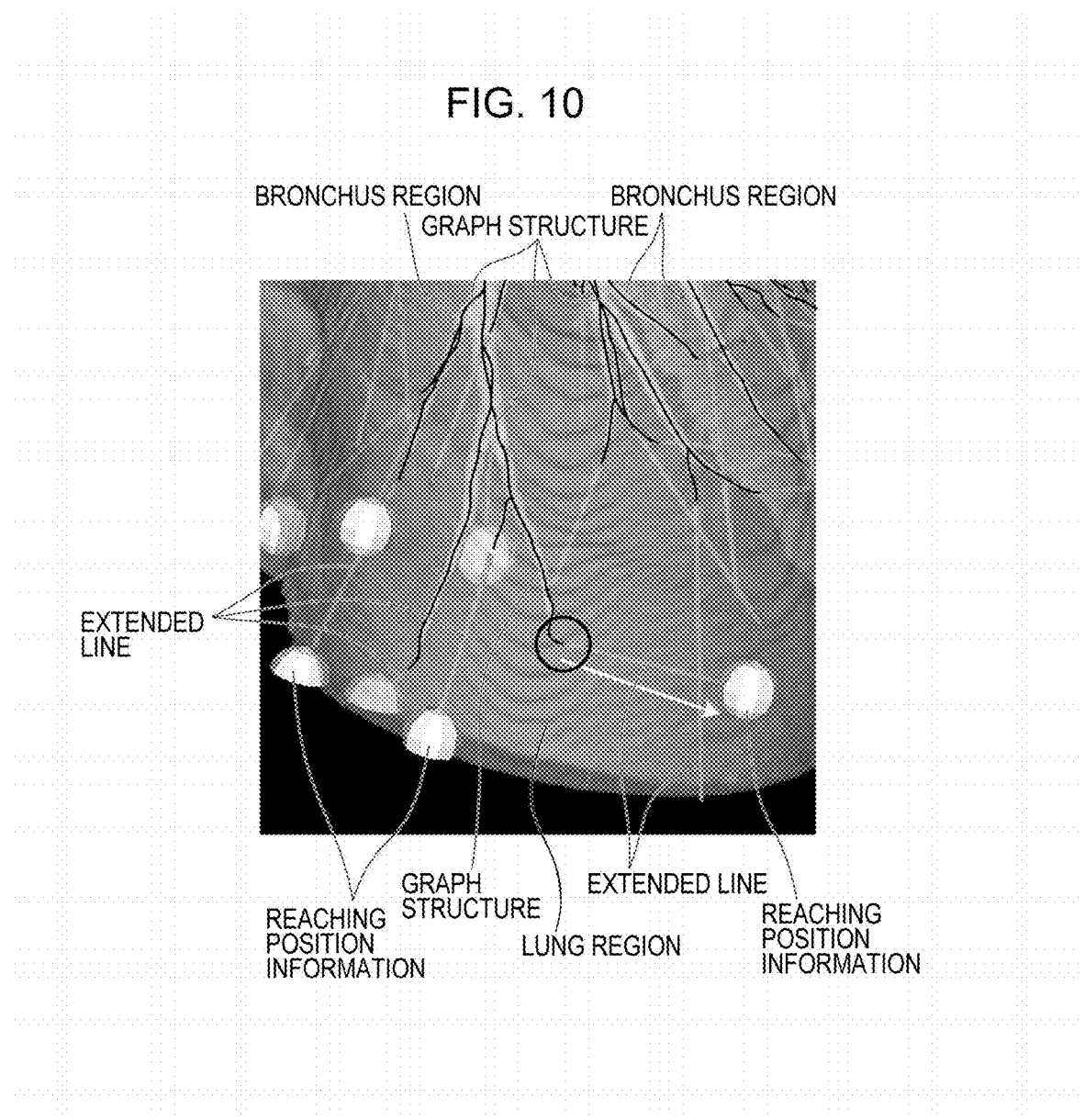
FIG. 10 is a diagram illustrating a case where an end of a graph structure acquired from the bronchus region is an irregular shape.

FIG. 10 is a diagram illustrating a case where the end of a branch of a graph structure has an irregular shape as described above. A portion near the end of the graph structure in a black-line circle illustrated in FIG. 10 is extracted to have a shape that bends to the right in the figure compared with the actual shape. As a result, the position at which the dye is estimated to reach is shifted to the right (in a direction of a white arrow) in the figure compared with the position at which the dye actually reaches.

Figure 11:
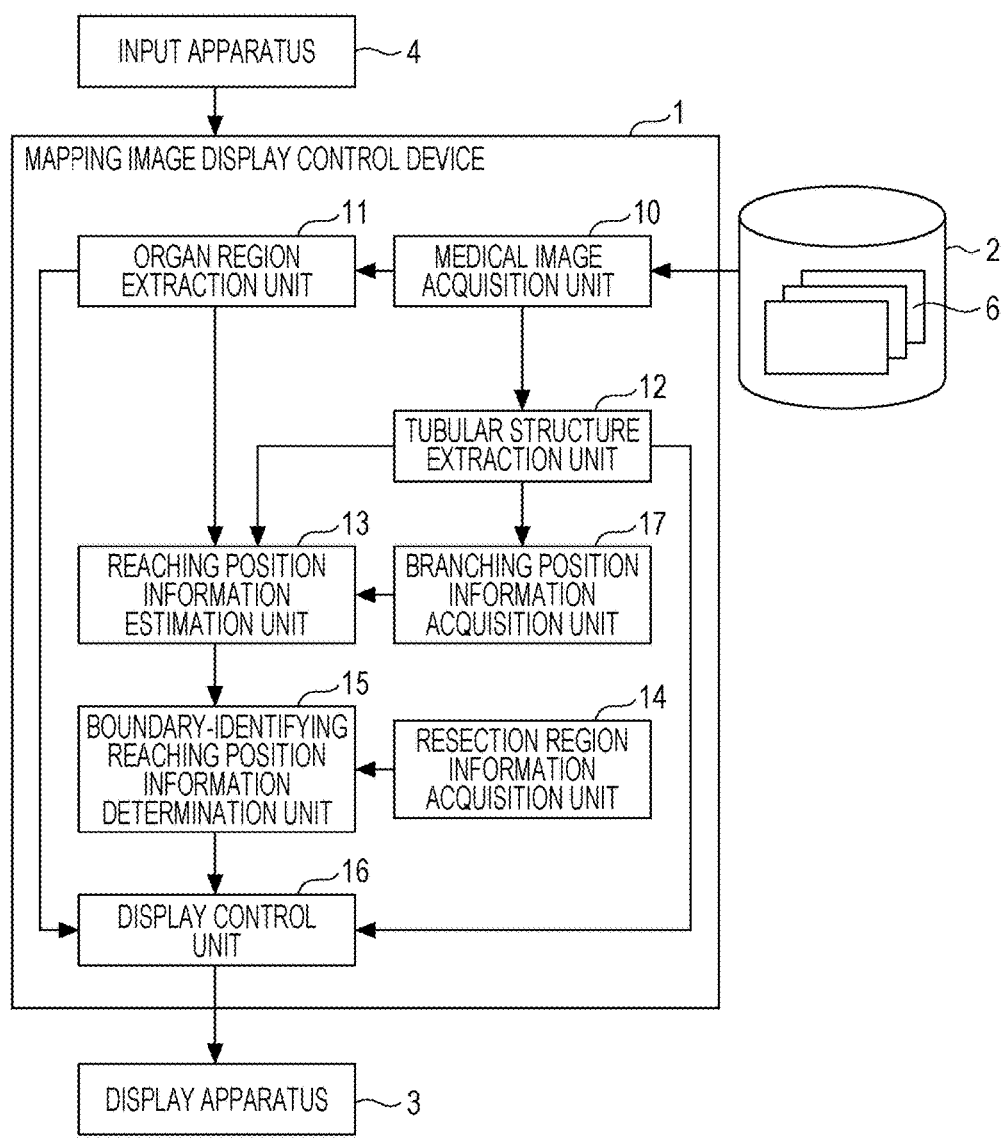
FIG. 11 is a block diagram illustrating a modification of the medical-image-diagnosis assisting system that uses an embodiment of the mapping image display control device, method, and computer readable non-transitory recording medium storing a program according to the present invention.

Accordingly, a branching position information acquisition unit 17 may be further provided in the mapping image display control device 1 as illustrated in FIG. 11. A straight line that is set on the basis of information about a branching position acquired by the branching position information acquisition unit 17 and the end of a branch of a graph structure may be estimated as an extended line of the branch of the bronchus region.

The branching position information acquisition unit 17 classifies a graph structure of a bronchus region extracted by the tubular structure extraction unit 12 into a start point, an end point, a branching point, and an edge and acquires position information of the branching point as information about the branching position of the bronchus region.

Figure 12:
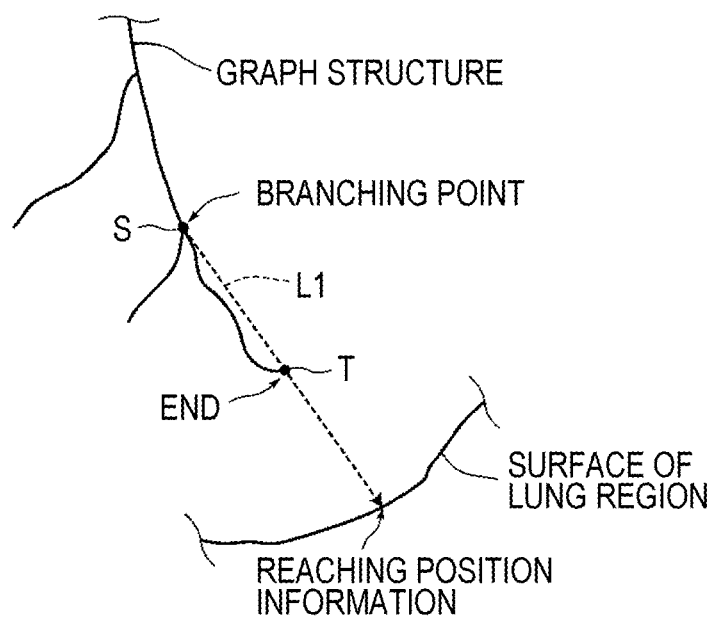
FIG. 12 is a diagram for describing a case where a straight line that links an end of a branch of a graph structure of a bronchus region and the first branching point from the end is estimated as an extended line of the branch of the bronchus region.

Specifically, the reaching position information estimation unit 13 estimates a straight line that links an end T of a branch of a graph structure of a bronchus region and a first branching point S from the end T as an extended line L1 of the branch of the bronchus region as illustrated in FIG. 12. The reaching position information estimation unit 13 then acquires the intersection of the extended line L1 and the surface of the lung region as a piece of reaching position information. The first branching point S from the end T refers to the first branch in a direction from the end of the bronchus region to the upstream side of the bronchus.

Although the first branching point S from the end T is used in the embodiment, the branching point to be used is not limited to this one. The second or third branching point from the end T may be used. In addition, although the end T of the branch of the graph structure of the bronchus region is linked to the first branching point S from the end T in the embodiment, the branching point S need not necessarily be used. Any point near the branching point S may be used as long as substantially the same result is obtained with the point. That is, a straight line that is set on the basis of the information about the branching position and the end of the branch of the graph structure includes a straight line that is set by linking the end T of the branch and a point near the branching point S.

In the case where a piece of reaching position information about a position at which an extended line of a branch included in a bronchus region reaches the surface of the lung region is estimated on the basis of information about a branching position as described above, the position which the dye reaches can be simulated at a high accuracy even if the extraction accuracy of the graph structure is low and the end of the graph structure bends in an unnatural direction as described above.

In addition, a mapping image in which pieces of reaching position image that are simulated at a high accuracy are mapped to the surface of the lung region can be generated and displayed.

In addition, since a straight line that links the end T and the first branching point S from the end T is estimated as the extended line L1 of the branch of the bronchus region, the extended line L1 can be estimated by a simple calculation process.

Figure 13:
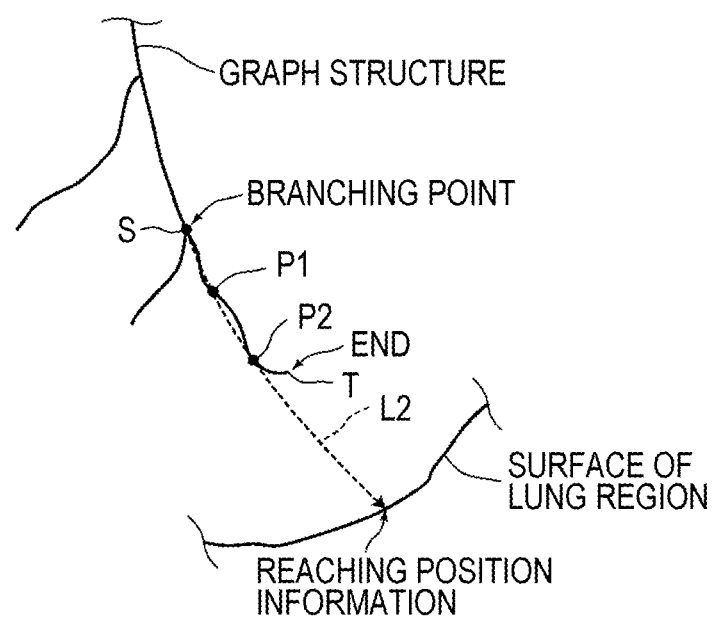
FIG. 13 is a diagram for describing a case where a curved line obtained by performing spline interpolation using two points on a branch and a branching point is estimated as an extended line of the branch of the bronchus region.

In the description above, a straight line that links an end of a graph structure and a branching point is estimated as an extended line of the branch of the bronchus region. However, the method for setting an extended line of a branch of a bronchus region is not limited to this one. For example, as illustrated in FIG. 13, spline interpolation may be performed by using two points P1 and P2 on a branch and the first branching point S from the end T of the branch, and a curved line L2 determined by the spline interpolation may be estimated as an extended line of the branch of the bronchus region.

In the case where the curved line L2 determined by spline interpolation is estimated as the extended line of the branch of the bronchus region in this way, the extended line of the branch can be estimated at a higher accuracy.

Note that the branching point S need not necessarily be used also in the case where the extended line of the branch is estimated by spline interpolation in this manner. Any point near the branching point S may be used as long as substantially the same result is obtained with the point.

Figure 14:
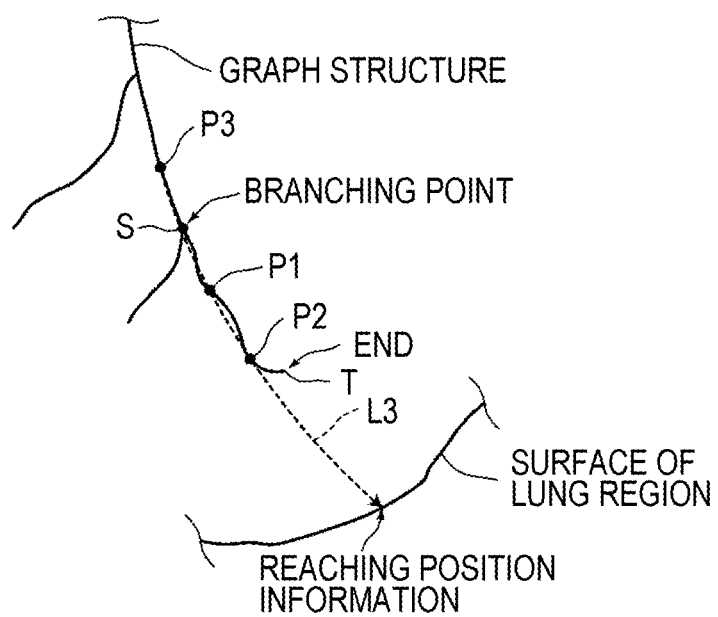
FIG. 14 is a diagram for describing another example of the case where the extended line of the branch of the bronchus region is estimated by spline interpolation.

In addition, in the description above, spline interpolation is performed by using the branching point S and the two points P1 and P2 on the branch. However, as for points other than the branching point S, three or more points may be set. In addition, instead of setting two points on the branch as illustrated in FIG. 13, spline interpolation may be performed by using at least one or more points P1 on the branch, the branching point S, and a point P3 located on the upstream side of the branching point S in the bronchus to estimate a curved line L3 as illustrated in FIG. 14. The point P3 is desirably set between the branching point S and a branching point that immediately precedes the branching point S on the upstream side in the bronchus. The points P1 to P3 used in spline interpolation may be set by the user in a given manner by using the input apparatus 4 or may be automatically set by setting a distance from the branching point S in advance.

Figure 15:
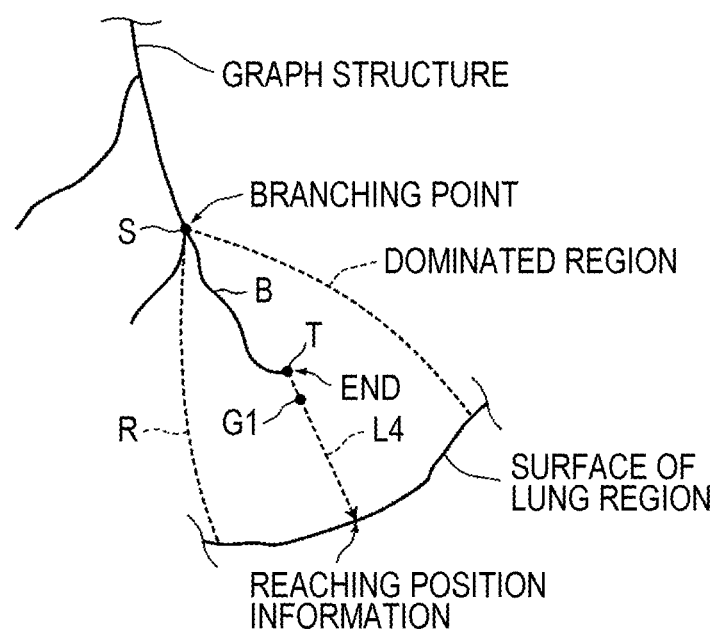
FIG. 15 is a diagram for describing a case where a straight line that links the centroid of a dominated region of a branch and an end of the branch is estimated as an extended line of the branch of the bronchus region.

In addition, a branch may be identified on the basis of information about a branching position acquired by the branching position information acquisition unit 17, a dominated region of the identified branch in the lung region may be identified, and a straight line that links the centroid of the dominated region and the end of the branch may be estimated as an extended line of the branch of the bronchus region. Specifically, as illustrated in FIG. 15, a branch B may be identified on the basis of the branching point S acquired by the branching position information acquisition unit 17, a dominated region R of the branch B in the lung region may be identified, and a straight line L4 that links a centroid G1 of the dominated region R and the end T of the branch B may be estimated as an extended line of the branch of the bronchus region. Note that a dominated region of a branch is set in advance for each branch from the anatomical viewpoint, and the centroid G1 in this case is a centroid of the dominated region having a three-dimensional shape in a three-dimensional space.

In the case where the straight line L4 that links the centroid G1 of the dominated region R and the end T of the branch B is estimated as the extended line of the branch of the bronchus region, the extended line of the branch can be estimated at a higher accuracy in accordance with the anatomical viewpoint.

Figure 16:
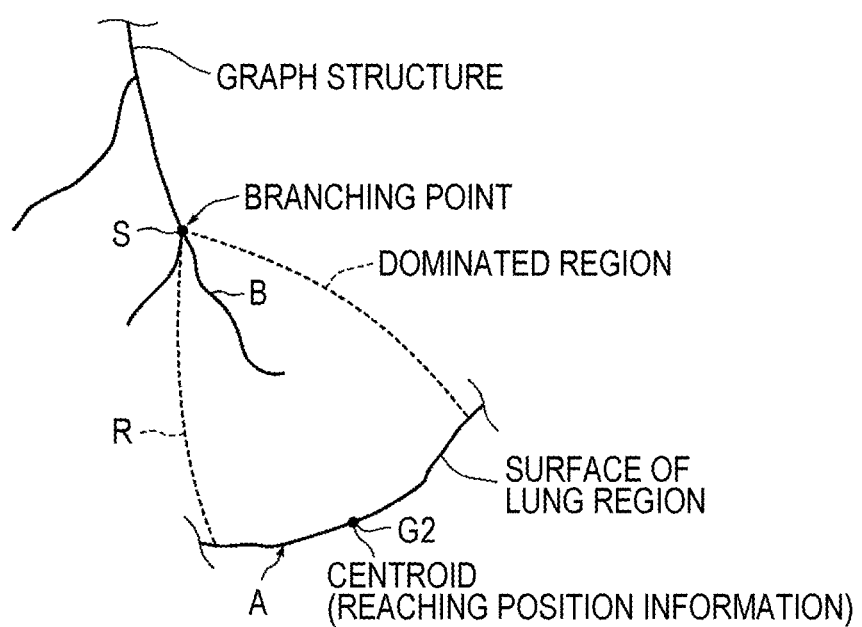
FIG. 16 is a diagram for describing a case where the centroid of a region that is the surface of the dominated region and that also is the surface of the lung region is estimated as a piece of reaching position information.

In addition, as another method for estimating a reaching position at which an extended line of a branch reaches the lung surface by using a dominated region of the branch of the bronchus region, the centroid of a region that is the surface of the dominated region of the branch and that also is the surface of the lung region may be estimated as a piece of reaching position information, for example. Specifically, as illustrated in FIG. 16, the branch B may be identified on the basis of the branching point S acquired by the branching position information acquisition unit 17, the dominated region R of the branch B in the lung region may be identified, and a centroid G2 of a region A that is the surface of the dominated region R and that also is the surface of the lung region may be estimated as a piece of reaching position information. Note that the centroid G2 in this case is a centroid of the region A that is represented as a plane in the three-dimensional space.

In addition, it is known that the pulmonary artery and the pulmonary vein are located near the bronchi and extending directions of the bronchi and extending directions of the pulmonary artery and the pulmonary vein are similar to each other. Thus, a position at which an extended line of a branch in a bronchus region reaches the lung surface may be estimated on the basis of information about the extending direction of the pulmonary artery or the pulmonary vein.

Figure 17:
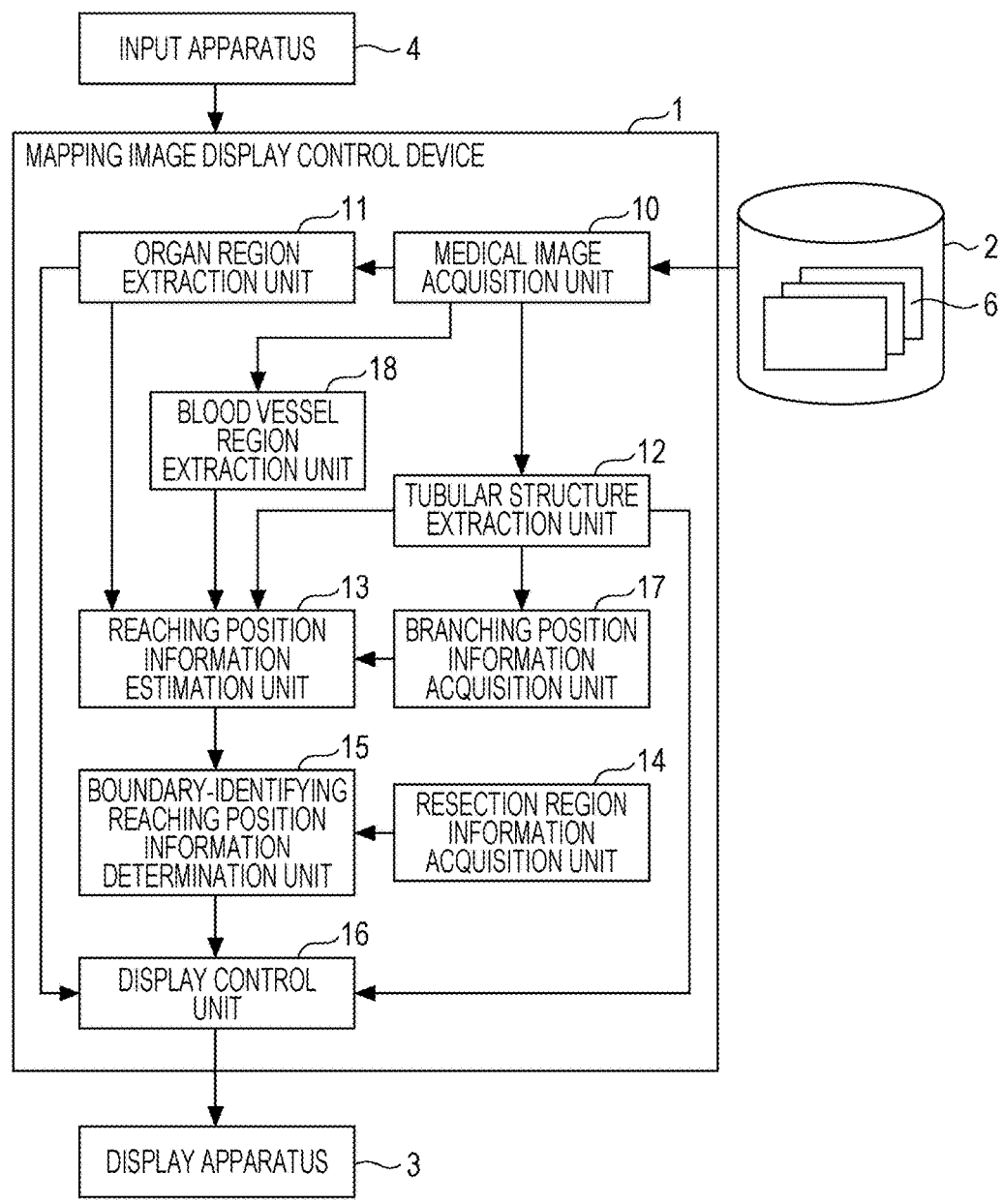
FIG. 17 is a block diagram illustrating a schematic configuration of the medical-image-diagnosis assisting system that further includes a blood vessel region extraction unit.

Specifically, a blood vessel region extraction unit 18 is further provided in the mapping image display control device 1 as illustrated in FIG. 17. The blood vessel region extraction unit 18 extracts a blood vessel region included in the lung region from the three-dimensional image 6. Specifically, the blood vessel region extraction unit 18 extracts a pulmonary artery region and a pulmonary vein region. As an extraction method of the pulmonary artery region and the pulmonary vein region, a publicly know technique, for example, a region growing method, can be used.

Figure 18:
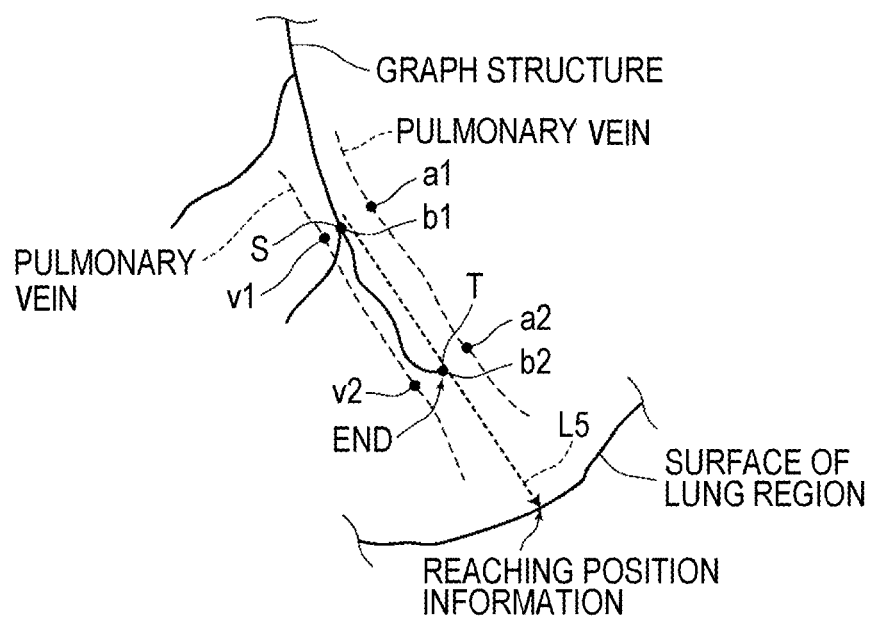
FIG. 18 is a diagram for describing a case where a position at which an extended line of a branch of a bronchus region reaches the lung surface is estimated on the basis of a blood vessel region and information about a branching position.

Then, the reaching position information estimation unit 13 identifies a pulmonary artery region and a pulmonary vein region that extend along a branch of a bronchus region on the basis of information about a branching position acquired by the branching position information acquisition unit 17 and estimates an extended line of the branch of the bronchus region on the basis of the identified pulmonary artery region and pulmonary vein region. Specifically, as illustrated in FIG. 18, a position v1 in a pulmonary artery region that is the closest to the branching point S acquired by the branching position information acquisition unit 17 and a position a1 in a pulmonary vein region that is the closest to the branching point S are detected. Further, a position v2 in the pulmonary artery region that is the closest to the end T of the branch of the graph structure and a position a2 in the pulmonary vein region that is the closest to the end T are detected.

The branching point S is the first branching point from the end T of the branch of the graph structure on the upstream side in the bronchus. In addition, the position v1 in the pulmonary artery region that is the closest to the branching point S is a position whose distance to the branching point S is the shortest in the pulmonary artery region, and the position a1 in the pulmonary vein region that is the closest to the branching point S is a position whose distance to the branching point S is the shortest in the pulmonary vein region. In addition, the position v2 in the pulmonary artery region that is the closest to the end T is a position whose distance to the end T is the shortest in the pulmonary artery region, and the position a2 in the pulmonary vein region that is the closest to the end T is a position whose distance to the end T is the shortest in the pulmonary vein region.

Then, a direction from the position v1 to the position v2 in the pulmonary artery region is estimated as an extending direction of the pulmonary artery region, and a first vector is set. A direction from the position a1 to the position a2 in the pulmonary vein region is estimated as an extending direction of the pulmonary vein region, and a second vector is set. An average of the first vector and the second vector is calculated. Then, a straight line L5 obtained by extending the average vector is estimated as the extended line of the branch of the bronchus region, and the position at which this extended line reaches the lung surface is acquired.

By estimating an extended line of a branch by using the pulmonary vein region and the pulmonary artery region in this way, the extended line of the branch can be estimated at a higher accuracy in accordance with the anatomical viewpoint.

In the description above, the first vector is set by using the positions v1 and v2 in the pulmonary artery region and the second vector is set by using the positions a1 and a2 in the pulmonary vein region. Alternatively, for example, spline interpolation may be performed by using the positions v1 and v2 in the pulmonary artery region and a point between these positions to set a first curved line, and spline interpolation may be performed by using the positions a1 and a2 in the pulmonary vein region and a point between these positions to set a second curved line. An average curved line of the first curved line and the second curved line may be estimated as the extended line of the branch of the bronchus region.

In addition, in the description above, an extended line of a branch is estimated by using both the pulmonary vein region and the pulmonary artery region. However, the extended line of the branch may be estimated by using only one of the pulmonary vein region and the pulmonary artery region. For example, a straight line that is parallel to the first vector set on the basis of the pulmonary artery region and that passes through the end T of the branch may be estimated as the extended line of the branch. Alternatively, a straight line that is parallel to the second vector set on the basis of the pulmonary vein region and that passes through the end T of the branch may be estimated as the extended line of the branch.

Note that in the embodiment described above, the medical image acquisition unit 10 acquires a three-dimensional image of the thorax of a patient, the organ region extraction unit 11 extracts a lung region from the three-dimensional image, and the tubular structure extraction unit 12 extracts a bronchus region included in the lung region. However, the target organ of the present invention is not limited to the lung and may be the liver. That is, the medical image acquisition unit 10 may acquire a three-dimensional image of the abdomen of a patient, the organ region extraction unit 11 may extract a liver region from the three-dimensional image, and the tubular structure extraction unit 12 may extract a blood vessel region included in the liver region. Note that a process performed after the tubular structure extraction unit 12 extracts a blood vessel region is substantially the same as that of the embodiment above. In this case, positions at which dye seeps to the liver surface if the dye is sprayed to the peripheries of the blood vessels are simulated, and a mapping image in which the positions are superimposed on the surface of the liver region can be displayed on the display apparatus 3.

REFERENCE SIGNS LIST 1 mapping image display control device
2 medical image storage server
3 display apparatus
4 input apparatus
10 medical image acquisition unit
11 organ region extraction unit
12 tubular structure extraction unit
13 reaching position information estimation unit
14 resection region information acquisition unit
15 boundary-identifying reaching position information determination unit
16 display control unit
17 branching position information acquisition unit
18 blood vessel region extraction unit

What is claimed is:

1. A mapping image display control device comprising:
an organ region extraction unit that extracts an organ region included in a three-dimensional image;
a tubular structure extraction unit that extracts a tubular structure included in the organ region;
a reaching position information estimation unit that estimates pieces of reaching position information each of a position at which an extended line of a branch included in the tubular structure reaches a surface of the organ region;
a resection region information acquisition unit that acquires information of a resection region in the organ region;
a boundary-identifying reaching position information determination unit that determines pieces of boundary-identifying reaching position information used to identify a boundary of the resection region from among the pieces of reaching position information based on the information of the resection region; and
a display control unit that generates a mapping image in which the pieces of boundary-identifying reaching position information are mapped to the surface of the organ region and that causes a display unit to display the mapping image.

2. The mapping image display control device according to claim 1, wherein the boundary-identifying reaching position information determination unit determines pieces of reaching position information of positions located in a previously set range from the boundary of the resection region on the surface of the organ region as the pieces of boundary-identifying reaching position information.

3. The mapping image display control device according to claim 1, wherein the boundary-identifying reaching position information determination unit determines a predetermined number of pieces of reaching position information in ascending order of distance from the boundary of the resection region on the surface of the organ region as the pieces of boundary-identifying reaching position information.

4. The mapping image display control device according to claim 3, wherein the boundary-identifying reaching position information determination unit determines pieces of reaching position information of positions located inside the resection region as the pieces of boundary-identifying reaching position information.

5. The mapping image display control device according to claim 1, wherein the boundary-identifying reaching position information determination unit determines, as the pieces of boundary-identifying reaching position information, three or more pieces of reaching position information for which an area of a polygonal shape formed by linking positions indicated by the three or more pieces of reaching position information is the largest among pieces of reaching position information of positions located inside the resection region on the surface of the organ region.

6. The mapping image display control device according to claim 1, wherein the resection region information acquisition unit extracts a lesion region included in the organ region and acquires the information of the resection region based on the lesion region.

7. The mapping image display control device according to claim 2, wherein the resection region information acquisition unit extracts a lesion region included in the organ region and acquires the information of the resection region based on the lesion region.

8. The mapping image display control device according to claim 3, wherein the resection region information acquisition unit extracts a lesion region included in the organ region and acquires the information of the resection region based on the lesion region.

9. The mapping image display control device according to claim 1, wherein the resection region information acquisition unit determines a dominated region of a branch included in the tubular structure and acquires the information of the resection region based on the dominated region.

10. The mapping image display control device according to claim 2, wherein the resection region information acquisition unit determines a dominated region of a branch included in the tubular structure and acquires the information of the resection region based on the dominated region.

11. The mapping image display control device according to claim 3, wherein the resection region information acquisition unit determines a dominated region of a branch included in the tubular structure and acquires the information of the resection region based on the dominated region.

12. The mapping image display control device according to claim 1, wherein the display control unit sets a region including a reaching position identified by each of the pieces of boundary-identifying reaching position information, generates a mapping image in which the region is mapped to the surface of the lung region, and causes the display unit to display the mapping image.

13. The mapping image display control device according to claim 2, wherein the display control unit sets a region including a reaching position identified by each of the pieces of boundary-identifying reaching position information, generates a mapping image in which the region is mapped to the surface of the lung region, and causes the display unit to display the mapping image.

14. The mapping image display control device according to claim 3, wherein the display control unit sets a region including a reaching position identified by each of the pieces of boundary-identifying reaching position information, generates a mapping image in which the region is mapped to the surface of the lung region, and causes the display unit to display the mapping image.

15. The mapping image display control device according to claim 1, wherein the organ region is a lung region, and the tubular structure is a bronchus region.

16. The mapping image display control device according to claim 2, wherein the organ region is a lung region, and the tubular structure is a bronchus region.

17. The mapping image display control device according to claim 1, further comprising:
   a branching position information acquisition unit that acquires information of a branching position of the tubular structure,
   wherein the reaching position information estimation unit estimates each of the pieces of reaching position information based on the information of the branching position.

18. The mapping image display control device according to claim 2, further comprising:
   a branching position information acquisition unit that acquires information of a branching position of the tubular structure,
   wherein the reaching position information estimation unit estimates each of the pieces of reaching position information based on the information of the branching position.

19. A mapping image display control method comprising:
   extracting an organ region included in a three-dimensional image;
   extracting a tubular structure included in the organ region;
   estimating pieces of reaching position information each of a position at which an extended line of a branch included in the tubular structure reaches a surface of the organ region;
   acquiring information of a resection region in the organ region;
   determining pieces of boundary-identifying reaching position information used to identify a boundary of the resection region from among the pieces of reaching position information based on the information of the resection region; and
   generating a mapping image in which the pieces of boundary-identifying reaching position information are mapped to the surface of the organ region and causing a display unit to display the mapping image.

20. A computer readable non-transitory recording medium storing a mapping image display control program causing a computer to function as:
   an organ region extraction unit that extracts an organ region included in a three-dimensional image;
   a tubular structure extraction unit that extracts a tubular structure included in the organ region;
   a reaching position information estimation unit that estimates pieces of reaching position information each of a position at which an extended line of a branch included in the tubular structure reaches a surface of the organ region;
   a resection region information acquisition unit that acquires information of a resection region in the organ region;
   a boundary-identifying reaching position information determination unit that determines pieces of boundary-identifying reaching position information used to identify a boundary of the resection region from among the pieces of reaching position information based on the information of the resection region; and a display control unit that generates a mapping image in which the pieces of boundary-identifying reaching position information are mapped to the surface of the organ region and that causes a display unit to display the mapping image.

* * * * *